United States Patent
McLane et al.

(10) Patent No.: US 9,546,194 B2
(45) Date of Patent: Jan. 17, 2017

(54) AMINOSTEROIDS FOR THE TREATMENT OF A PTP1B ASSOCIATED DISEASE

(71) Applicant: Ohr Pharmaceutical Inc., New York, NY (US)

(72) Inventors: Michael McLane, Lansdale, PA (US); Inez Ruiz-White, Mount Laurel, NJ (US); W. Lee Maloy, Lansdale, PA (US); Henry R. Wolfe, Glenmoore, PA (US)

(73) Assignee: Ohr Pharmaceutical, Inc., New York, NY (US)

( * ) Notice: Subject to any disclaimer, the term of this patent is extended or adjusted under 35 U.S.C. 154(b) by 0 days.

(21) Appl. No.: 14/394,789

(22) PCT Filed: Apr. 19, 2013

(86) PCT No.: PCT/US2013/037330
§ 371 (c)(1),
(2) Date: Oct. 16, 2014

(87) PCT Pub. No.: WO2013/158970
PCT Pub. Date: Oct. 24, 2013

(65) Prior Publication Data
US 2015/0099727 A1 Apr. 9, 2015

Related U.S. Application Data

(60) Provisional application No. 61/636,252, filed on Apr. 20, 2012.

(51) Int. Cl.
*C07J 41/00* (2006.01)
*C07J 43/00* (2006.01)

(52) U.S. Cl.
CPC .......... *C07J 41/0005* (2013.01); *C07J 41/005* (2013.01); *C07J 41/0055* (2013.01); *C07J 43/003* (2013.01)

(58) Field of Classification Search
None
See application file for complete search history.

(56) References Cited

U.S. PATENT DOCUMENTS

| | | | |
|---|---|---|---|
| 5,856,535 A | 1/1999 | Zasloff et al. | |
| 7,074,778 B2 * | 7/2006 | Levitt | A61K 31/56 514/169 |
| 2010/0324004 A1 | 12/2010 | McLane et al. | |

FOREIGN PATENT DOCUMENTS

| | | |
|---|---|---|
| WO | 96/40151 A1 | 12/1996 |
| WO | 01/19830 A1 | 3/2001 |
| WO | 01/19831 A1 | 3/2001 |
| WO | 01/42273 A2 | 6/2001 |
| WO | 2009/032321 A2 | 3/2009 |

OTHER PUBLICATIONS

Johnson, A. W. Invitation to Organic Chemistry 1999 Jones and Bartlett: Mississauga, Canada, p. 24.*
Shu "The synthesis of spermine analogs of the shark aminosterol squalmine." Steroids, 2002, 67(3,4), 291-304.*
Jones "The synthesis and characterization of analogs of the antimicrobial compound squalmine:6_-hydroxy-3-aminosterols synthesized from hyodeoxycholic acid" Steroids 1996, 61, 565-571.*
Korean Office Action issued on Nov. 20, 2015 by the Korean Intellectual Property Office (KIPO) in corresponding Korean Patent Application No. 10-2014-7031485, with an English-langage translation.
International Search Report issued in corresponding International Patent Application No. PCT/US2013/037330 dated Oct. 15, 2013.

\* cited by examiner

*Primary Examiner* — David K O'Dell
(74) *Attorney, Agent, or Firm* — Morgan, Lewis & Bockius LLP

(57) ABSTRACT

This application is directed to the use of aminosteroid compounds for the selective inhibition of the enzyme PTP1B in a mammal for the treatment of diabetes.

10 Claims, No Drawings

AMINOSTEROIDS FOR THE TREATMENT OF A PTP1B ASSOCIATED DISEASE

CROSS REFERENCE TO RELATED APPLICATIONS

This application is technically related to U.S. Pat. No. 5,856,535 which issued Jan. 5, 1999 and U.S. published Application No. 2010-0324004, which was filed Sep. 8, 2008. Both documents are incorporated by reference in their entirety.

FIELD OF THE INVENTION

This application is directed to the use of aminosteroid compounds for the selective inhibition of the enzyme PTP1B in a mammal for the treatment of a PTP1B associated disease such as diabetes.

BACKGROUND OF THE INVENTION

Protein phosphorylation is a well-recognized cellular mechanism for transducing and regulating signals during different stages of cellular function (see, e.g., Hunter, Phil, Trans. R. Soc. Lond. B. 353: 583-605 (1998); Chan et al., Annu. Rev. Immunol. 12: 555-592 (1994); Zhang, Curr. Top. Cell. Reg. 35: 21-68 (1997); Matozaki and Kasuga, Cell. Signal. 8: 113-119 (1996)). There are at least two major recognized classes of phosphatases: (1) those that dephosphorylate proteins that contain a phosphate group(s) on a serine or threonine moiety (termed Ser/Thr phosphatases or dual specificity phosphatases (DSPs)) and (2) those that remove a phosphate group(s) from the amino acid tyrosine (termed protein tyrosine phosphatases (PTPases or PTPs)).

Several studies clearly indicate that the activity of the auto-phosphorylated Insulin-Induced Receptor Tyrosine Kinase (IRTK) can be reversed by dephosphorylation in vitro (reviewed in Goldstein, Receptor 3: 1-15 (1993)) with the tri-phosphorylated tyrosine-1150 domain being the most sensitive target for PTPases. This tri-phosphorylated tyrosine-1150 domain appears to function as a control switch of IRTK activity and the IRTK appears to be tightly regulated by PTP-mediated dephosphorylation in vivo (Faure et al., J. Biol. Chem. 267: 11215-11221 (1992)).

PTP1B has been identified as at least one of the major phosphatases involved in IRTK regulation through studies conducted both in vitro (Seely et al., Diabetes 45: 1379-1385 (1996)) and in vivo using PTP1B neutralizing antibodies (Ahmad et al., J. Biol. Chem. 270: 20503-20508 (1995)). Three independent studies have indicated that PTP1B knock-out mice have increased glucose tolerance, increased insulin sensitivity and decreased weight gain when on a high fat diet (Elchebly et al., Science 283: 1544-1548 (1999), Klaman et al., Mol. Cell. Biol. 20: 5479-5489 (2000), and Bence et al., Nature Med (2006)). Overexpression or altered activity of tyrosine phosphatase PTP1B can contribute to the progression of various disorders, including, insulin resistance and diabetes (Ann. Rev. Biochem. 54: 897-930 (1985)). Furthermore, there is evidence which suggests that inhibition of protein tyrosine phosphatase PTP1B is therapeutically beneficial for the treatment of disorders such as type I and II diabetes, obesity, autoimmune disorders, acute and chronic inflammation and osteoporosis (Zhang Z. Y. et al., Expert Opin. Investig. Drugs 2: 223-33 (2003); Taylor S. D. et al., Expert Opin. Investig. Drugs 3:199-214 (2004); J. Natl. Cancer Inst. 86: 372-378 (1994); Mol. Cell. Biol. 14: 6674-6682 (1994); The EMBO J. 12: 1937-1946 (1993); J. Biol. Chem. 269: 30659-30667 (1994); and Biochemical Pharmacology 54: 703-711(1997)).

The PTPase family of enzymes can be classified into two subgroups: (1) intracellular or non-transmembrane PTPases and (2) receptor-type or transmembrane PTPases. Most known intracellular type PTPases contain a single conserved catalytic phosphatase domain consisting of 220-240 amino acid residues. The regions outside the PTPase domains are believed to play important roles in localizing the intracellular PTPases subcellularly (Mauro, L. J. and Dixon J. E., TIBS 19: 151-155 (1994)). The first of the intracellular PTPases to be purified and characterized was PTP1B (Tonks et al., J. Biol. Chem. 263: 6722-6730 (1988)). Other examples of intracellular PTPases include (1) T-cell PTPase (TCPTP) (Cool et al., Proc. Natl. Acad. Sci. USA 86: 5257-5261 (1989)), (2) neuronal phosphatases STEP (Lombroso et al., Proc. Natl. Acad. Sci. USA 88: 7242-7246 (1991)), (3) PTP1C/SH-PTP1/SHP-1 (Plutzky et al., Proc. Natl. Acad. Sci. USA 89: 1123-1127 (1992)), (4) PTP1D/Syp/SH-PPT2/SHP-2 (Vogel et al., Science 259: 1611-1614 (1993); Feng et al., Science 259: 1607-1611(1993)).

Receptor-type PTPases consist of (a) a putative ligand-binding extracellular domain, (b) a transmembrane segment, and (c) an intracellular catalytic region. The structure and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PTPases have two tandemly duplicated catalytic PTPase domains. The first PTPase receptor subtypes identified were (1) CD45 (Ralph, S. J., EMBO J. 6: 1251-1257 (1987)) and (2) LAR (Streuli et al., J. Exp. Med. 168:1523-1530 (1988)). Since then, many more receptor subtypes have been isolated and characterized, including, e.g., PTPalpha, PTPbeta, PTPdelta, PTPepsilon and PTPxi. (Krueger et al. EMBO J. 9: 3241-3252 (1990)).

Although agents have been identified for use as PTP1B inhibitors, such as the heteroaryl- and aryl-amino acetic acids described in WO 01/19831, WO 01/19830, and WO 01/17516, these agents do not exhibit separation of the inhibitory activity between PTP1B and TCPTP. Furthermore, because of the potential immunosuppressive effects resulting from inhibiting TCPTP, selective inhibition of PTP1B over TCPTP would make such agents more suitable for drug development as they could diminish or eliminate undesired side effects resulting from such nonselectivity.

Therefore, there is a need for a drug that can selectively inhibit PTP1B. In addition, if neuronal PTP1B is inhibited, rapid weight loss can be induced in obese individuals, thus also treating the effects of obesity, preventing neurodegeneration or Alzheimer's. A drug of this type would be useful for the treatment of complications due to obesity, obesity in type II diabetes, high serum cholesterol, sleep apnea (especially in pickwickian syndrome), nonalcoholic steatohepatitis and surgery for obese patients.

SUMMARY OF THE INVENTION

The present invention relates to various aminosteroids which inhibit protein phosphatase IB (PTP1B). The invention also relates to compositions which contain these aminosteroids, such as pharmaceutically acceptable compositions, and methods of their use to treat PTP1B related diseases in mammals, particularly humans.

One aspect of the invention relates to aminosteroid compounds that are inhibitors of the enzyme PTP1B of the following formula, or a pharmaceutically acceptable salt thereof:

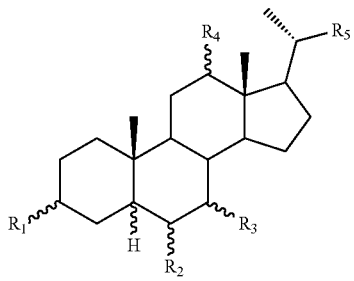

wherein:
R$_1$=—NH(CH$_2$)$_{1-4}$—NH—R$_6$, H,

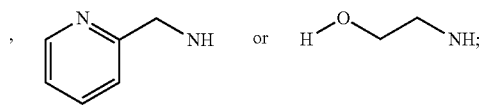

R$_6$=—(CH$_2$)$_{1-4}$—NH—R$_7$ or —(CH$_2$)$_{0-3}$—C$_1$-C$_5$ alkyl or —(CH$_2$)$_{0-3}$—C$_3$-C$_7$ cycloalkyl or —(CH$_2$)$_{0-3}$—C$_3$-C$_6$ heterocycloalkyl or —(CH$_2$)$_{0-3}$-aromatic or —(CH$_2$)$_{0-3}$-heteroaromatic or H;

R$_7$=—(CH$_2$)$_{1-4}$—NH$_2$ or —(CH$_2$)$_{1-4}$—NH—(C$_1$-C$_5$ alkyl) or —(CH$_2$)$_{14}$—NH—(C$_3$-C$_6$ heterocycloalkyl) or —(CH$_2$)$_{1-4}$—NH-aromatic or —(CH$_2$)$_{1-4}$—NH-heteroaromatic or H;

R$_2$=—OH or H;
R$_3$=—OH or NH—R$_8$ or methylsulfone or methyl sulfide or H;
R$_8$=acetyl, —SO$_2$—CH$_3$ or —C(O)OCH$_3$;
R$_4$=—OH or H;

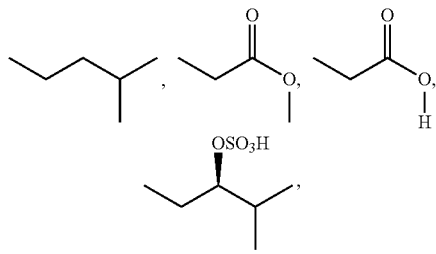

R$_5$=

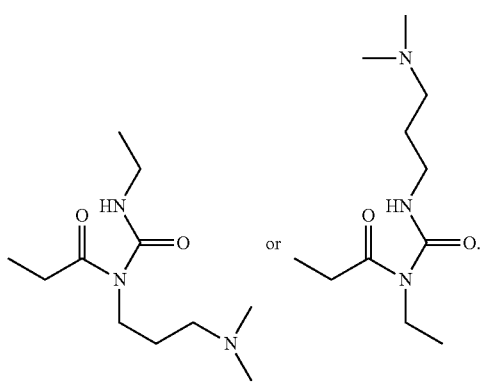 [SMILES: CCNC(=O)N(CCCN(C)C)C(=O)CC ; CCC(=O)N(CC)C(=O)NCCCN(C)C]

In an exemplary embodiment of the invention, the compound is of the above formula wherein

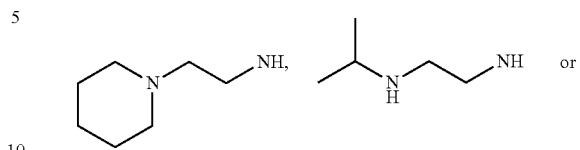

R$_1$=

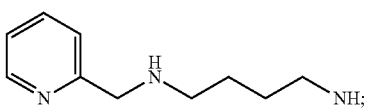

R$_3$=—OH or —NH—SO$_2$CH$_3$; and
R$_5$=

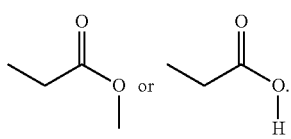

An embodiment of the invention relates to aminosteroid compounds that are inhibitors of the enzyme PTP1B of the following formula, or a pharmaceutically acceptable salt thereof

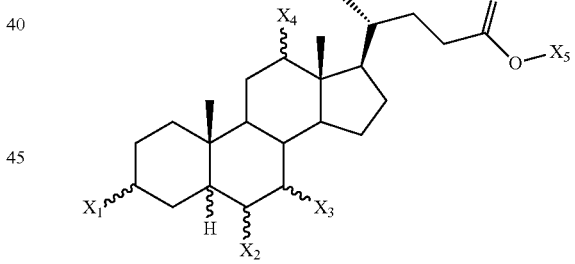

wherein:
X$_1$=

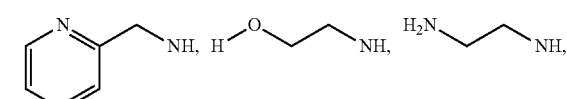

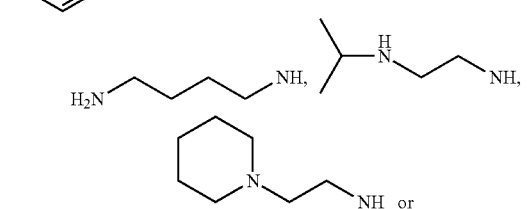

-continued

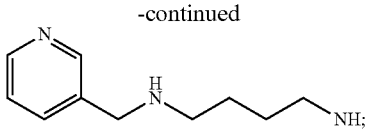

$X_2$=—OH or H;
$X_3$=H, —OH, -S(O)$_2$—CH$_3$, —NHC(O)—CH$_3$, —NHC(O)—OCH$_3$, —NHC(O)—SCH$_3$, —NH—SO$_2$CH$_3$ or —SCH$_3$;
$X_4$=—OH or H; and
$X_5$=H or —CH$_3$.

An embodiment of the invention relates to aminosteroid compounds that are inhibitors of the enzyme PTP1B of the following formula, or a pharmaceutically acceptable salt thereof

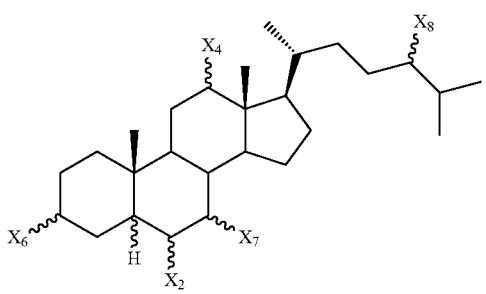

wherein:
$X_6$=

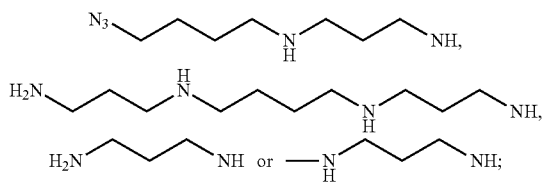

$X_2$=—OH or H;
$X_7$=—OH or H;
$X_4$=—OH or H; and
$X_8$=—OH or H.

The bond represented as ∿ in all chemical structures depicted herein is intended to represent both stereoisomeric positions of the bond at that particular carbon atom—i.e., a ⋯ bond and a ▬ bond.

Another aspect of the invention is a compound selected from the specific compounds listed in Table 1, or a pharmaceutically acceptable salt thereof.

Another aspect of the invention is a pharmaceutical composition comprising a compound selected from any of the above depicted formulae or a specific compound listed in Table 1, and a diluent or carrier.

Another aspect of the invention is a method for treating a disorder in a mammal mediated by inhibition of protein tyrosine phosphatase PTP1B comprising administering to a mammal in need thereof a therapeutically effective amount of a compound selected from any of the above depicted formulae or a specific compound of Table 1.

In exemplary embodiments, the disorder treated by administration of a compound of any of the above depicted formulae or a specific compound of Table 1 includes, but is not limited to, obesity in type II diabetes, high serum cholesterol, sleep apnea and nonalcoholic steatohepatitis.

DETAILED DESCRIPTION OF THE INVENTION

The compounds encompassed by the above formula and the compounds listed in Table 1 are intended to include all pharmaceutically acceptable salts of the listed compounds. In addition, where the stereochemistry at any given carbon atom is undefined, it is intended that each individual stereoisomer is encompassed as well as the racemic mixture. For representing stereochemistry in chemical structures, a bold line indicates a bond coming out of the plane of the paper, while a hashed line indicates a bond going into the plane of the paper.

As defined herein, alkyl includes, but is not limited to, straight chain and branched hydrocarbons, such as, methyl, ethyl, propyl, isobutyl and isopropyl.

As defined herein, cycloalkyl includes, but is not limited to, cyclopropyl, cyclobutyl, cyclopentyl and cyclohexyl.

As defined herein, heterocycloalkyl includes, but is not limited to, piperidine, piperazine, tetrahydrofuran, dioxane, and morpholine.

As defined herein, aromatic includes, but is not limited to, benzene, naphthalene and anthracene.

As defined herein, heteroaromatic includes, but is not limited to, pyridine, furan, thiophene, pyrrole, oxazole, thiazole, isoxazole and imidazole.

The aminosteroids of the invention may be administered alone or as part of a pharmaceutical composition. Pharmaceutical compositions for use in vitro or in vivo in accordance with the present invention may be formulated in a conventional manner using one or more physiologically acceptable carriers comprising excipients and auxiliaries that facilitate processing of the active compounds into preparations which can be used pharmaceutically. Proper formulation is dependent upon the route of administration chosen. Examples of carriers or excipients include, but are not limited to, calcium carbonate, calcium phosphate, various sugars, starches, cellulose derivatives, gelatin and polymers such as polyalkylene glycols, including polyethylene glycols.

In addition to carriers, the pharmaceutical compositions of the invention may also optionally include stabilizers, preservatives and/or adjuvants. For examples of typical carriers, stabilizers and adjuvants known to those of skill in the art, see Remington: The Science and Practice of Pharmacy, Lippincott, Williams & Wilkins, 21$^{st}$ ed. (2005), which is incorporated by reference in its entirety.

Optionally, other therapies known to those of skill in the art may be combined with the administration of the aminosteroids of the invention. More than one aminosteroid may be present in a single composition.

In vivo administration of the aminosteroids of the invention can be effected in one dose, multiple doses, continuously or intermittently throughout the course of treatment. Doses range from about 0.01 mg/kg to about 10 mg/kg, such as between about 0.01 mg/kg to about 1 mg/kg, such as between about 0.1 mg/kg to about 1 mg/kg in single or divided daily doses. Methods of determining the most effective means and dosages of administration are well known to those of skill in the art and will vary with the composition used for therapy, the purpose of the therapy, the target cell being treated and the subject being treated. Single or multiple administrations can be carried out with the dose level and pattern being selected by the treating physician.

Pharmaceutical compositions containing the aminosteroids of the invention can be administered by any suitable route, including oral, rectal, intranasal, topical (including transdermal, aerosol, ocular, buccal and sublingual), parenteral (including subcutaneous, intramuscular and intravenous), intraperitoneal and pulmonary. It will be appreciated that the preferred route will vary with the condition and age of the recipient, and the particular disease being treated.

For oral administration, the aminosteroids of the invention can be formulated readily by combining them with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as maize starch, wheat starch, rice starch, potato starch, gelatin, gum tragacanth, methyl cellulose, hydroxypropylmethylcellulose, sodium carboxymethylcellulose and polyvinylpyrrolidone (PVP). If desired, disintegrating agents may be added, such as the cross-linked polyvinyl pyrrolidone, agar, alginic acid or a salt thereof, such as sodium alginate.

For administration by inhalation, the aminosteroids of the present invention are conveniently delivered in the form of an aerosol spray presentation from pressurized packs or a nebulizer, with the use of a suitable propellant (e.g., 1,1,1, 2-tetrafluoroethane), carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The aminosteroids can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as buffers, bacteriostats, suspending agents, stabilizing agents, thickening agents, dispersing agents or mixtures thereof.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides or liposomes. Aqueous injection suspensions may contain substances that increase the viscosity of the suspension, such as sodium carboxymethyl cellulose, sorbitol or dextran. Optionally, the suspension may also contain suitable stabilizers or agents that increase the solubility of the compounds to allow for the preparation of highly concentrated solutions. In an exemplary embodiment, the aminosteroids of the invention are dissolved in a 5% sugar solution, such as dextrose, before being administered parenterally.

For injection, the aminosteroids of the invention may be formulated in aqueous solutions, such as in physiologically compatible buffers such as Hanks's solution, Ringer's solution or physiological saline buffer. For transmucosal administration, penetrants appropriate to the barrier to be permeated are used in the formulation. Such penetrants are generally known in the art.

The aminosteroids may also be formulated in rectal compositions such as suppositories or retention enemas, e.g., containing conventional suppository bases such as cocoa butter or other glycerides.

The aminosteroids may also be combined with at least one additional therapeutic agent.

Without further description, it is believed that one of ordinary skill in the art can, using the preceding description and the following illustrative examples, make and utilize the compounds of the present invention and practice the claimed methods. The following working examples illustrate particular embodiments of the present invention, and are not to be construed as limiting in any way the overall disclosure of the invention.

EXAMPLES

Example 1

Inhibition of PTP1B by Aminosteroid Analogues

The aminosteroid analogues were tested for inhibition against the commercially available full length tyrosine phosphatase PTP1B. The ability of each analogue to inhibit the activity of PTP1B was measured in the presence of 5 µM of the aminosteroid analogue. The assay uses para-nitro-phenyl phosphate (pNPP), a non-specific substrate to assess phosphatase activity. Phosphatase activity was based on the ability of PTP1B to catalyze the hydrolysis of pNPP to p-nitrophenol (pNP). The activity was measured using a single point spectrophometric absorbance at 405 nm (the absorbance of the chromogenic product, para-nitrophenol (pNP). The percent inhibition of tyrosine phosphatase activity by the aminosteroid analogues was determined by the fractional response of pNP formation in the presence of inhibitor over the maximal response of pNP formation observed in the absence of inhibitor. The results of these assays are shown in Table 1, and show many analogues that cause greater than 50% inhibition at 5 µM concentration.

Example 2

Inhibition of TCPTP by Aminosteroid Analogues

The aminosteroid analogues were also tested for their ability to inhibit the tyrosine phosphatase TCPTP as an indication of their potential toxicity by the inhibition of the immune response. The TCPTP inhibition assay was done in the same manner as the PTP1B assay except full length TCPTP was used as the enzyme and the inhibitor was at a concentration of 200 µM. The results of the TCPTP inhibition assays are shown in Table 1, column 4 and show three compounds that inhibit TCPTP less than 50% even at a 20 fold greater concentration.

Example 3

Effect of Aminosteroid Analogues on Body Weight, Blood Glucose Levels and the Oral Glucose Tolerance Test (OGTT) in the Diabetic Mouse To determine in vivo efficacy of the aminosteroid analogues an ob/ob (Lep$^{ob}$) mouse model was used. Ob/ob mice are extensively used for screening of antidiabetic and/or anti-obesity agents. Ob/ob mice were treated with either saline or 5 or 10 mg/kg aminosteroid analogue every 3 days for a total of 4 doses via ip injection. Body weight, glucose tolerance and fasting blood glucose levels were measured for each group during the study. Each group had at least an N of 4 animals. All reagents and lab animals are commercially available.

Starting at study day 0, body weight measurements were taken every day for each group for up to 30 days. Percent change in body weight was calculated as the fractional response of body weight on study day X over the original body weight on study day 0. Animals displaying a reduction in body weight suggest that the aminosteroid analogue inhibits neuronal PTP1B as has been shown for MSI-1436 (U.S. patent application Ser. No. 12/676,701). Table 1, column 7 shows % change in body weight for the aminosteroids tested in vivo. In spite of their ability to inhibit PTP1B in vitro, they were not able to produce weight loss, suggesting that they may not interact with neuronal PTP1B.

On study day 13, all animal groups were fasted overnight. On study day 14, 25 μL of whole blood was collected and analyzed for the glucose level (mg/dL) using a glucose analyzer. No significant reduction of fasting blood glucose (FBG) levels compared to saline control was seen in any of the aminosteroids tested in vivo Table 1, column 6.

On study day 14, an oral glucose tolerance test (OGTT) was performed to assess glucose tolerance. At time 0, an oral glucose challenge (1.5 g/kg) was administered by oral gavage. At time points 0, 15, 30, 60, 90, and 120 min post glucose load, 25 μl of whole blood was withdrawn from the tail vein of the animal and the glucose level was measured using a glucose analyzer. The glucose concentration vs time was plotted and the above baseline area under the curve (AbAUC) of the glucose excursion time curve was determined using trapezoidal rule analyses. A significant reduction ($p<0.05$) in AbAUC compared to saline control is shown for MSI-2520, -2527, -2507, -2511, -2510 and -2532 as seen in Table 1, column 5.

TABLE 1

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2522 | | 104 | 50 | NA | NA | NA |
| 2526 | | 104 | NA | NA | NA | NA |
| 2520 | | 103 | 19 | −30.1 | 34.7 | 0.5 |

TABLE 1-continued

| MSI # | Compound | PTP1B % Inhib. at (5 µM) | TCPTP % Inhib. at (200 µM) | AbAUC % Change From Saline | FBG % Change From Saline | % BW Nader |
|---|---|---|---|---|---|---|
| 2521 | | 103 | 67 | NA | NA | NA |
| 2524 | | 103 | 15 | NA | NA | NA |
| 2518 | | 102 | 12 | NA | NA | NA |
| 2519 | | 102 | 26 | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2527 | | 102 | 15 | −33.0 | 32.2 | 0.0 |
| 2523 | | 101 | 8 | NA | NA | NA |
| 2514 | | 96 | 30 | −11.6 | 9.2 | −1.5 |
| 2507 | | 94 | −11 | −45.8 | −9.4 | 1.4 |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2511 | | 93 | 0 | −34.6 | 5.1 | −0.9 |
| 2512 | | 90 | −2 | −5.8 | 45.8 | 0.4 |
| 2515 | | 89 | 19 | NA | NA | NA |
| 2528 | | 75 | 2 | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2510 | | 72 | 23 | −32.9 | 12.0 | 1.6 |
| 2529 | | 64 | 4 | NA | NA | NA |
| 2506 | | 60 | 60 | NA | NA | NA |
| 2516 | | 56 | 25 | NA | NA | NA |
| 1436 | | 54 | 0 | −55.9 | −51.3 | −52.6 |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2532 | (structure) | 53 | 4 | −56.6 | −0.7 | −0.8 |
| 2517 | (structure) | 51 | 11 | NA | NA | NA |
| 2531 | (structure) | 48 | 1 | NA | NA | NA |
| 2530 | (structure) | 46 | 1 | NA | NA | NA |
| 2504 | (structure) | 43 | 22 | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2505 | | 39 | NA | NA | NA | NA |
| 2500 | | 0 | NA | NA | NA | NA |
| 2501 | | 0 | NA | NA | NA | NA |
| 2502 | | 0 | NA | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2503 | | NA | NA | NA | NA | NA |
| 2508 | | NA | NA | NA | NA | NA |
| 2509 | | NA | NA | NA | NA | NA |
| 2513 | | NA | NA | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2525 | | NA | NA | NA | NA | NA |
| 2533 | | NA | 5 | NA | NA | NA |
| 2534 | | NA | 0 | NA | NA | NA |
| 2535 | | NA | 8 | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2536 | | NA | NA | NA | NA | NA |
| 2537 | | NA | NA | NA | NA | NA |
| 2538 | | NA | NA | NA | NA | NA |
| 2539 | | NA | NA | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2540 | | NA | NA | NA | NA | NA |
| 2541 | | NA | NA | NA | NA | NA |
| 2542 | | NA | NA | NA | NA | NA |
| 2543 | | NA | NA | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2544 | (structure) | NA | NA | NA | NA | NA |
| 2545 | (structure) | NA | NA | NA | NA | NA |
| 2546 | (structure) | NA | NA | NA | NA | NA |
| 2547 | (structure) | NA | NA | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2548 | | NA | NA | NA | NA | NA |
| 2549 | | NA | NA | NA | NA | NA |
| 2550 | | NA | NA | NA | NA | NA |
| 2551 | | NA | NA | NA | NA | NA |
| 2552 | | NA | NA | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2553 | | NA | NA | NA | NA | NA |
| 2554 | | NA | NA | NA | NA | NA |
| 2555 | | NA | NA | NA | NA | NA |
| 2556 | | NA | NA | NA | NA | NA |

TABLE 1-continued

| MSI # | Compound | PTP1B % Inhib. at (5 μM) | TCPTP % Inhib. at (200 μM) | AbAUC % Change From Saline | FBG % Change From Saline | % BW Nader |
|---|---|---|---|---|---|---|
| 2557 | | NA | NA | NA | NA | NA |
| 2558 | | NA | NA | NA | NA | NA |

The invention claimed is:

1. A compound or pharmaceutically acceptable salt thereof selected from the group consisting of:

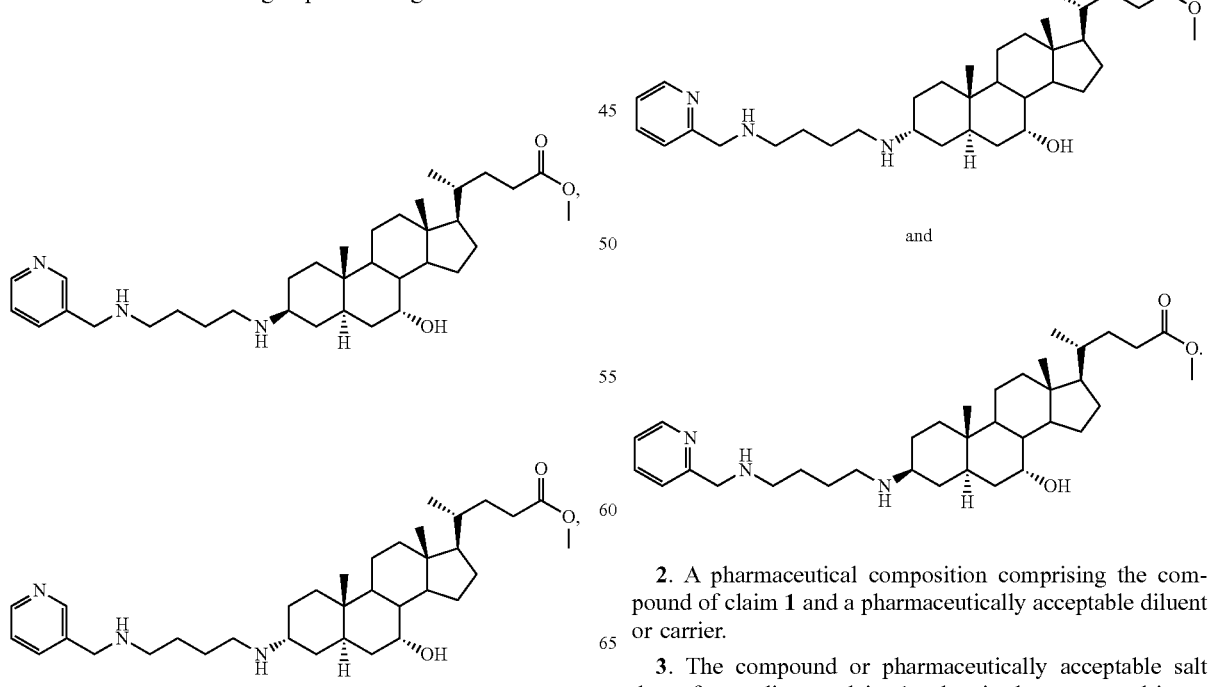

and

2. A pharmaceutical composition comprising the compound of claim 1 and a pharmaceutically acceptable diluent or carrier.

3. The compound or pharmaceutically acceptable salt thereof according to claim 1, wherein the compound is

4. The compound or pharmaceutically acceptable salt thereof according to claim 1, wherein the compound is

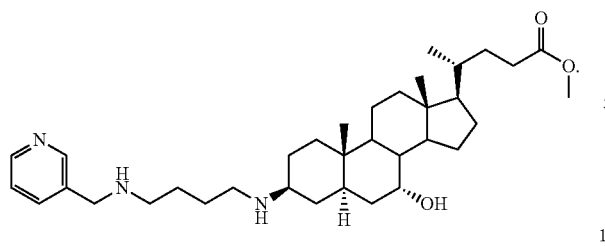

5. A pharmaceutical composition comprising the compound of claim 3 and a pharmaceutically acceptable diluent or carrier.

6. A pharmaceutical composition comprising the compound of claim 4 and a pharmaceutically acceptable diluent or carrier.

7. The compound or pharmaceutically acceptable salt thereof according to claim 1, wherein the compound is

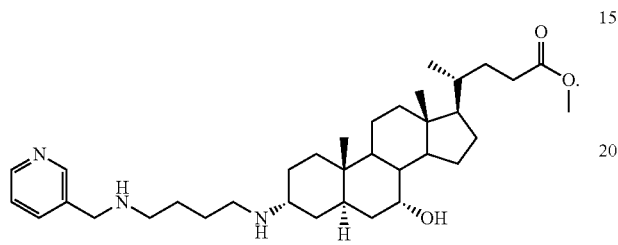

8. The compound or pharmaceutically acceptable salt thereof according to claim 1, wherein the compound is

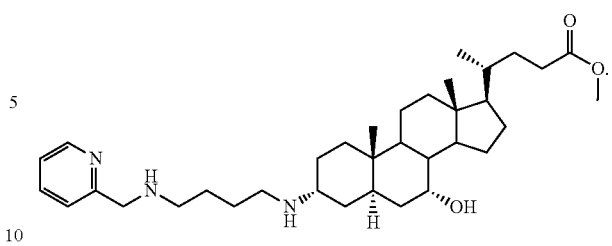

9. A pharmaceutical composition comprising the compound of claim 7 and a pharmaceutically acceptable diluent or carrier.

10. A pharmaceutical composition comprising the compound of claim 8 and a pharmaceutically acceptable diluent or carrier.

* * * * *